(12) United States Patent
Gilder et al.

(10) Patent No.: US 10,610,413 B2
(45) Date of Patent: Apr. 7, 2020

(54) EARTIP

(75) Inventors: Stephen D. Gilder, San Clemente, CA (US); David B. Mulvey, San Diego, CA (US)

(73) Assignee: HONEYWELL SAFETY PRODUCTS USA, INC., Smithfield, RI (US)

(*) Notice: Subject to any disclaimer, the term of this patent is extended or adjusted under 35 U.S.C. 154(b) by 315 days.

(21) Appl. No.: 12/784,970

(22) Filed: May 21, 2010

(65) Prior Publication Data

US 2010/0300461 A1 Dec. 2, 2010

Related U.S. Application Data

(60) Provisional application No. 61/180,759, filed on May 22, 2009.

(51) Int. Cl.
*A61F 11/10* (2006.01)
*A61F 11/08* (2006.01)
(Continued)

(52) U.S. Cl.
CPC .......... *A61F 11/08* (2013.01); *B29C 44/3442* (2013.01); *C08J 9/0061* (2013.01); *C08J 9/28* (2013.01); *B29C 44/02* (2013.01); *C08J 2203/06* (2013.01); *C08J 2205/05* (2013.01); *C08J 2207/10* (2013.01); *C08J 2375/04* (2013.01); *C08J 2421/00* (2013.01); *C08J 2427/00* (2013.01)

(58) Field of Classification Search
CPC .......... A61F 11/00; A61F 11/06; A61F 11/08; A61F 11/10; B29C 44/02; B29C 44/3442; C08J 9/28; C08J 9/0061; C08J 2203/06; C08J 2205/05; C08J 2207/10; C08J 2375/04; C08J 2421/00; C08J 2427/00
USPC .................. 128/864, 866–868; 181/128–130, 181/134–135
See application file for complete search history.

(56) References Cited

U.S. PATENT DOCUMENTS 3,574,429 A * 4/1971 Reising ................. F16C 23/045
264/54
3,579,640 A 5/1971 Beguin et al.
(Continued)

FOREIGN PATENT DOCUMENTS

AU 2010219362 B8 2/2014
CA 2714900 C 8/2017
(Continued)

OTHER PUBLICATIONS

PCT International Search Report dated Jul. 28, 2010; International Application No. PCT/US2010/035835, citing relevant documents, 5 pages.
(Continued)

*Primary Examiner* — Anna K Kinsaul
*Assistant Examiner* — Camtu T Nguyen
(74) *Attorney, Agent, or Firm* — Wick Phillips Gould & Martin, LLP

(57) ABSTRACT

An improved EarTip may result from the distribution of PTFE throughout a slow recovery foam. Such an EarTip may have a finer, more uniform cell structure that aids in insertion within a user's ear canal. It may also have a smoother skin, with a lower kinetic coefficient of friction, and may provide improved sound attenuation.

10 Claims, 2 Drawing Sheets

(51) Int. Cl.
  *B29C 44/34* (2006.01)
  *C08J 9/28* (2006.01)
  *C08J 9/00* (2006.01)
  *B29C 44/02* (2006.01)

(56) References Cited

U.S. PATENT DOCUMENTS

| | | | | |
|---|---|---|---|---|
| 3,624,190 | A | * | 11/1971 | Cekada et al. .................. 264/41 |
| 3,674,720 | A | * | 7/1972 | Dunn ........................... 521/176 |
| 3,811,437 | A | * | 5/1974 | Gardner, Jr. ............ A61F 11/10 |
| | | | | 128/864 |
| 3,846,523 | A | | 11/1974 | Geerdes |
| 3,846,532 | A | | 11/1974 | Kubitzker et al. |
| 3,931,381 | A | * | 1/1976 | Lindberg ..................... 264/45.5 |
| 4,158,087 | A | * | 6/1979 | Wood ................. C08G 18/4833 |
| | | | | 521/137 |
| 4,160,449 | A | * | 7/1979 | Wade ........................... 128/864 |
| 4,215,683 | A | | 8/1980 | Lundin et al. |
| 4,338,929 | A | | 7/1982 | Lundin et al. |
| 4,569,950 | A | * | 2/1986 | Hoshi et al. ..................... 521/88 |
| 4,774,938 | A | * | 10/1988 | Leight ..................... A61F 11/14 |
| | | | | 128/864 |
| 4,806,186 | A | | 2/1989 | Sirkin et al. |
| 5,002,151 | A | | 3/1991 | Oliveria et al. |
| 5,250,579 | A | | 10/1993 | Smits et al. |
| 5,254,600 | A | * | 10/1993 | Blanpied et al. ............. 521/125 |
| 5,792,998 | A | | 8/1998 | Gardner, Jr. et al. |
| 5,954,229 | A | | 9/1999 | Scholey et al. |
| 5,957,136 | A | | 9/1999 | Magidson et al. |
| 6,001,890 | A | * | 12/1999 | Hamilton ..................... 521/128 |
| 6,241,120 | B1 | | 6/2001 | Scholey et al. |
| 6,310,961 | B1 | * | 10/2001 | Oliveira et al. ............. 381/328 |
| 6,408,981 | B1 | * | 6/2002 | Smith et al. .................. 181/126 |
| 6,759,443 | B2 | * | 7/2004 | Brant et al. ..................... 521/51 |
| 8,061,472 | B2 | * | 11/2011 | Tiemens ....................... 181/135 |
| 2006/0175722 | A1 | | 8/2006 | Babcock et al. |
| 2008/0181441 | A1 | | 7/2008 | Smith |

FOREIGN PATENT DOCUMENTS

| | | |
|---|---|---|
| CN | 102481207 B | 6/2016 |
| EP | 0870487 B1 | 6/2004 |
| EP | 2432435 | 3/2012 |
| FR | 2815248 | 10/2000 |
| GB | 906796 | 9/1962 |
| GB | 1572844 | 8/1980 |
| JP | 63257558 A | 10/1988 |
| JP | H08503720 A | 4/1996 |
| JP | 2004509786 A | 4/2004 |
| JP | 5738281 B2 | 6/2015 |
| WO | 9203112 | 3/1992 |
| WO | 0226465 A1 | 4/2004 |
| WO | 2010135688 A1 | 11/2010 |

OTHER PUBLICATIONS

PCT Written Opinion of the International Searching Authority; dated Jul. 28, 2010; International Application No. PCT/US2010/035835, 7 pages.
PCT International Preliminary Report on Patentability; dated Dec. 1, 2011 ; International Application No. PCT/US2010/035835, 8 pages.
Examination Report dated Aug. 30, 2013; Australia Patent Application No. 2010219362, 4 pages.
Notice of Acceptance dated Oct. 24, 2013; Australia Patent Application No. 2010219362, 2 pages.
Office Action dated Apr. 22, 2016; Canada Patent Application No. 2,714,900, 3 pages.
Notice of Allowance dated Jan. 11, 2017; Canada Patent Application No. 2,714,900, 1 page.
Communication pursuant to Rules 161(1) and 162 EPC dated Jan. 1, 2012, Europe Patent Application No. 10721067.6, 2 pages.
Notification of Reasons of Refusal dated Feb. 27, 2014; Japan Patent Application No. 2012-512070, 7 pages.
Notification of Reasons of Refusal dated Aug. 27, 2014; Japan Patent Application No. 2012-512070, 5 pages.
Notice of Allowance dated Mar. 23, 2015; Japan Patent Application No. 2012-512070, 6 pages.
Office Action dated Jul. 24, 2013, China Patent Application No. 201080032958.9, 31 pages.
Office Action dated Mar. 13, 2014, China Patent Application No. 201080032958.9, 35 pages.
Decision on Rejection dated Sep. 30, 2014, China Patent Application No. 201080032958.9, 21 pages.
Office Action dated May 18, 2015 China Patent Application No. 201080032958.9, 10 pages.
Dffice Action dated Dec. 7, 2015 China Patent Application No. 201080032958.9, 12 pages.
Notification to grant Patent Right dated Mar. 15, 2016 China Patent Application No. 201080032958.9, 4 pages.
PT International Search Report dated Jul. 28, 2010; International Application No. PCT/US2010/035835, citing relevant documents, 5 pages.
Office Action dated Dec. 7, 2015 China Patent Application No. 201080032958.9, 12 pages.
Europe Patent Application No. 10721067.6, Examination Report, dated Nov. 10, 2017, 4 pages.

* cited by examiner

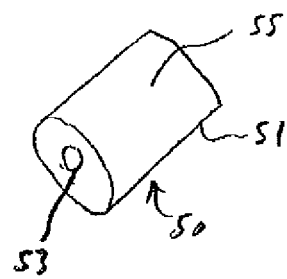
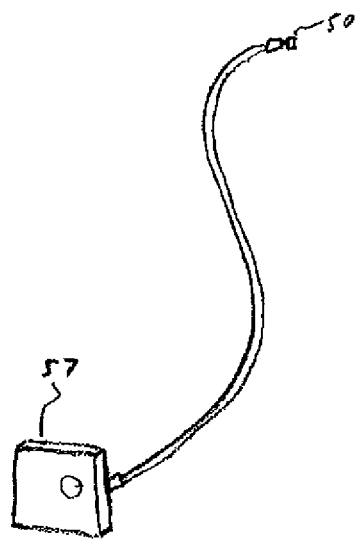

EARTIP

CROSS-REFERENCE TO RELATED APPLICATIONS

This application is related to and claims priority under 35 USC § 119 to U.S. Provisional Patent Application Ser. No. 61/180,759 entitled "Improved EarTip," filed May 22, 2009, which is hereby fully incorporated by reference as if reproduced in its entirety.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

Disclosed embodiments relate generally to hearing protection and/or sound transmission devices, and more specifically to earplugs and/or ear tips.

BACKGROUND

Applicants have found that for earplugs and ear tips, effective insertion may be important for proper and comfortable fit. Further, both earplugs and ear tips may need to be inserted properly within a user's ear canal in order to effectively isolate the user's ear canal from outside background noise. After all, the primary purpose of earplugs is to provide this type of auditory isolation, blocking potentially damaging sounds from entering the user's ear canal; and ear tips for sound transmission devices (such as portable music devices by way of nonexclusive example) work best if they can isolate the user's ear canal from outside background noise that would interfere with the user's ability to clearly hear the desirable sounds produced by the sound transmission device (for example, the music). Applicants have found that providing optimized acoustical seal may be important for the overall effectiveness of earplugs and/or ear tips. Applicants have further found that the acoustical seal may be impacted by the user's ability to properly insert the earplug and/or ear tip into position within the ear canal.

Further, Applicants have found that it may be useful for ear tips used with sound transmission devices to reduce any buildup of static electricity. If static electricity buildup from the sound transmission device grows too large, there could be some risk of an unpleasant shock to the user when the static electricity buildup does finally discharge. Thus, Applicants have found that an ear tip that reduces the static electricity buildup associated with some sound transmission devices may offer improved performance and user comfort.

SUMMARY

Applicants have developed an improved earplug/ear tip that in one or more embodiments may provide for one or more of the following: improved insertion, a finer, more uniform cell structure and/or a smoother surface skin, lower recovery pressure, improved sound attenuation, and/or reduced electro-static buildup. Generally, embodiments of the EarTip (which could be an earplug or an ear tip, by way of non-exclusive example) comprise slow recovery low resilient foam plastic material comprising a plurality of open cells, in which a low coefficient of friction additive is distributed throughout the foam material. In an embodiment, the slow recovery low resilient foam plastic material comprises slow recovery low resilient polyurethane foam (such as slow recovery latex-modified polyurethane foam, by way of non-exclusive example). And in some embodiments, the low coefficient of friction additive may comprise PTFE. In one embodiment, the EarTip comprises a main body portion having an outward form or shape constructed to enable its reception in an ear canal; wherein the main body is formed of pressure-molded slow recovery low resilient foam plastic material (such as a slow recovery latex-modified polyurethane foam, by way of non-exclusive example) comprising multiple gas-filled open cells and having an additive material possessing a low coefficient of friction (such as PTFE by way of non-exclusive example) distributed essentially uniformly throughout the foam material. While the foam material may optionally be molded in an open mold, in some embodiments the foam material would be molded under a pressure of at least about 0.5 psi in a closed mold. In an aspect, the polyurethane foam material may be formed by combining a prepolymer stream with a latex aqueous solution stream of about 60% solids; and the PTFE may comprise between about 2% and about 7% of the latex aqueous solution stream by weight. In an aspect, the PTFE may comprise about 4% of the latex aqueous solution stream by weight. In another aspect, the EarTip is an earplug.

In another embodiment, the EarTip comprises a main body portion having an outward form or shape constructed to enable its reception in an ear canal; wherein the main body is formed of pressure-molded slow recovery low resilient foam plastic material forming multiple gas-filled open cells and having a low coefficient of friction additive (such as PTFE by way of non-exclusive example) distributed throughout the foam material. In an aspect, the plastic material may be polyurethane foam. In another aspect, the EarTip is a passive hearing protection device, such as an earplug.

In yet another embodiment, the EarTip comprises a main body portion having an outer shape or form constructed to enable its reception in an ear canal, wherein the main body is formed of slow recovery low resilient polyurethane foam forming multiple cells and having a low coefficient of friction additive (such as PTFE by way of non-exclusive example) distributed throughout; the average diameter of the cells is smaller than that of comparable control devices/elements of slow recovery foam without the additive (which is often comprises PTFE); and the main body has a cross-section, wherein the average diameter of cells does not vary across the cross-section as much as for control devices without the additive (typically PTFE for example). In other words, the cell structure of the present EarTip embodiment (enhanced with PTFE) is finer and more uniform than Applicants found in similar slow recovery low resilient polyurethane foam control devices without PTFE during internal side-by-side comparison testing. In an aspect, the EarTip is an earplug.

In still another embodiment, the EarTip comprises a main body portion having an outer shape or form constructed to enable its reception in an ear canal, wherein the main body portion is formed of slow recovery foam (which may have a low coefficient of friction additive, such as PTFE for example, dispersed throughout); the main body portion has an average static coefficient of friction greater than that of standard slow recovery foam (for example, at least about 1.82, or alternatively 1.70); and the main body portion has an average kinetic coefficient of friction less than that of standard slow recovery foam (for example, no more than 1.32, or alternatively 1.47). In an aspect, the EarTip is an earplug.

In another embodiment, the EarTip comprises a main body portion of slow recovery low resilient foam plastic having an outward form or shape constructed to enable its reception in an ear canal and formed by providing a prepolymer stream and a latex aqueous solution stream; adding between about 2 to 7% by weight of low coefficient of friction additive (which might comprise PTFE for example) to the latex aqueous solution stream; and combining the prepolymer stream and the latex aqueous solution stream; wherein the latex aqueous solution stream is about 60% solids and combining the prepolymer stream and the latex aqueous solution stream occurs in a closed mold under pressure of at least about 0.5 psi. Alternatively, the foam could be formed in an open mold. In an aspect, the EarTip is an earplug. In aspects, this embodiment of the EarTip may have the coefficient of friction, PTFE distribution, and/or cell structure characteristics described above.

In yet another embodiment, an earplug comprises a main body portion having an outer surface shape constructed to enable its reception in an ear canal; wherein the main body is formed of pressure-molded slow recovery low resilient foam plastic material forming multiple gas-filled open cells and having PTFE distributed throughout the foam material. In an aspect, the plastic material may be polyurethane foam. In another aspect, wherein the main body is formed of pressure-molded slow recovery low resilient polyurethane foam material forming multiple gas-filled open cells and having PTFE distributed essentially uniformly throughout the foam material; the polyurethane foam material has been molded under a pressure of at least about 0.5 psi in a closed mold; the polyurethane foam material is formed by combining a prepolymer stream with a latex aqueous solution stream of about 60% solids; and the PTFE comprises between about 2% and about 7% of the latex aqueous solution stream by weight. In one aspect, the PTFE may comprise about 4% of the latex aqueous solution stream by weight.

In one aspect, the average diameter of the cells of the earplug is smaller than that of control devices of slow recovery foam without PTFE; and the main body has a cross-section, wherein the average diameter of cells does not vary across the cross-section as much as for control devices without PTFE. In other words, the cell structure of the present earplug embodiment (enhanced with PTFE) is finer and more uniform than Applicants found in similar slow recovery foam control devices without PTFE during internal side-by-side comparison testing. In still another aspect, the main body portion of the earplug has an average static coefficient of friction greater than that of standard slow recovery foam (for example, at least about 1.82, or alternatively 1.70); and the main body portion has an average kinetic coefficient of friction less than that of standard slow recovery foam (for example, no more than 1.21, or alternatively 1.47).

Another embodiment relates to a foam material formed of pressure-molded slow recovery low resilient foam plastic material comprising multiple gas-filled open cells and having a low coefficient of friction additive (such as PTFE for example) approximately uniformly distributed throughout the foam material. In one aspect, the foam may be formed by providing a prepolymer stream and a latex aqueous solution stream; adding between about 2 to 7% by weight PTFE to the latex aqueous solution stream; and combining the prepolymer stream and the latex aqueous solution stream; wherein the latex aqueous solution stream is about 60% solids and materials in the prepolymer stream and the latex aqueous solution stream foam under pressure in a closed mold. In one aspect, the foam may be formed into EarTips based on the shape of the mold.

In yet another embodiment, a method is disclosed for forming foam comprising the steps of: providing a prepolymer stream and a latex aqueous solution stream; adding between about 2 to 7% by weight of low coefficient of friction additive to the latex aqueous solution stream; and combining the prepolymer stream and the latex aqueous solution stream; wherein the latex aqueous solution stream is about 60% solids and materials in the prepolymer stream and the latex aqueous solution stream foam in a mold. In one aspect, the low coefficient of friction additive may comprise PTFE. In another aspect, combining the prepolymer stream and the latex aqueous solution stream occurs in a closed mold under pressure of at least about 0.5 psi. In yet another aspect, the foam comprises slow recovery latex-modified polyurethane foam. The mold may also be shaped to form the foam into an EarTip having a main body portion constructed to enable its reception in an ear canal.

Applicants also incorporate fully by reference U.S. Pat. No. 4,774,938, which provides additional details regarding slow recovery foam earplugs, to the extent that it does not contradict the specific details set forth herein. In the event that any information incorporated by reference does not mesh with the specific disclosure details set forth herein, the specific disclosure in this application shall govern.

BRIEF DESCRIPTION OF THE DRAWINGS

For a more complete understanding of the present disclosure, and for further details and optional advantages thereof, reference is now made to the accompanying drawings, wherein:

FIG. 3 is a perspective view of an ear tip for a sound transmission device of one embodiment of the improved EarTip; and FIG. 4 is a perspective view of an ear tip located on the sound tube stem of a sound transmission device.

DETAILED DESCRIPTION OF THE INVENTION

Figure 1:
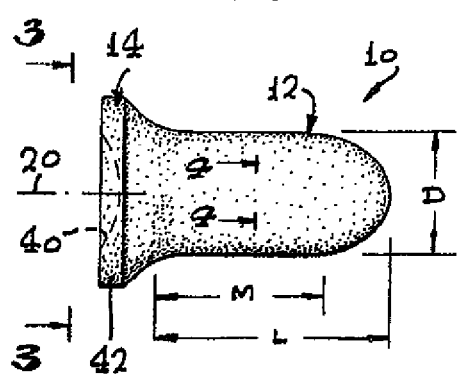
FIG. 1 is a side elevation view of an earplug showing one embodiment of an improved earplug.

The following brief definition of terms shall apply throughout the application:

The term "EarTip" generally refers to either an ear tip for use on a sound transmission device (such as an earbud for an communication headset or a portable music device, by way of non-exclusive example), or to an earplug for protecting the user's hearing, with the EarTip typically comprising a resilient portion designed to fit snugly in a user's ear canal;

The term "PTFE" generally means a low coefficient of friction material comprising polytetrafluoroethylene, such as Lubrizol 1765 or Teflon by way of non-exclusive example; PTFE may include additional additives as well, including wax by way of non-exclusive example;

The term "slow recovery low resilient foam plastic" generally refers to a conventional foam that has slow recovery properties, such that if the foam is compressed and then released, the foam returns back towards its original uncompressed state over a period of time (typically greater than 10 seconds but less than 30 minutes); one example of such a slow recovery low resilient foam plastic is slow recovery latex-modified polyurethane foam;

The term "sound transmission device" generally refers to any device for transmitting sound into a user's ear canal from an outside source, and by way of nonexclusive example may include personal music devices (such as an IPod™), a communication headset or earpiece, or a hearing aid;

The term "open cell" used when describing foam relates to a foam comprising a plurality of open cells (which for example might have only struts but no walls); in practice open cell foam may include both open and closed cells, with open cell foam typically having more open cells that a closed cell foam;

The term "comprising" means including but not limited to, and should be interpreted in the manner it is typically used in the patent context;

The phrases "in one embodiment," "according to one embodiment," and the like generally mean that the particular feature, structure, or characteristic following the phrase is included in at least one embodiment of the present invention, and may be included in more than one embodiment of the present invention (importantly, such phrases do not necessarily refer to the same embodiment); and If the specification states a component or feature "may," "can," "could," "should" or "might" be included or has a characteristic, that particular component or feature is not required to be included or to have the characteristic.

Generally, Applicants have found that a foam EarTip comprising a low coefficient of friction additive (which might comprise PTFE by way of non-exclusive example) distributed throughout the foam may result in a novel cell structure that provides beneficial properties. In some embodiments, the low coefficient of friction additive may comprise wax. Applicants have developed an EarTip which, in one embodiment, is comprised of a slow recovery low resilient foam plastic material forming multiple gas-filled open cells and having PTFE approximately uniformly distributed throughout the foam. The PTFE in this embodiment is not a mere surface treatment, but is dispersed throughout the foam's cell walls, and Applicants have found that this results in foam with a novel cell structure. In one embodiment the slow-recovery foam may be a slow recovery visco-elastic foam formed by adding latex (which may be synthetic latex) during the formation of a standard foam. By way of example, the foam may be formed of polyurethane in conjunction with latex (i.e. a slow recovery latex-modified polyurethane foam). Alone, polyurethane foam is a fast recovery foam, but the inclusion of latex may provide slow recovery properties to the foam. In forming EarTips of this embodiment, PTFE would also be approximately uniformly distributed throughout the foam. Thus, the EarTip would be comprised of a slow recovery low resilient foam plastic material having PTFE distributed throughout the cell wall structure.

Preferably, in one embodiment the EarTip may be comprised of pressure-molded polyurethane foam, which may be formed by mixing a prepolymer stream and a latex aqueous solution stream of about 60% solids. PTFE is added into the latex aqueous solution stream in a range of about 2% to about 7% by weight. In other words, between about 2% to about 7% by weight of the solids are removed from the latex stream and are replaced with PTFE. In one preferred embodiment, PTFE is added into the latex stream at about 4% by weight. At this level, the foam tends to have a recovery time of about 35 to 45 seconds. This results in a foam with slow recovery properties having PTFE essentially distributed uniformly throughout the foam. In alternative embodiments, other low coefficient of friction additives might be used in place of PTFE.

Figure 2:
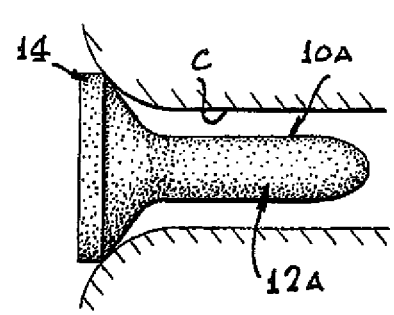
FIG. 2 is a side elevation view of a compressed earplug in condition for insertion into the ear canal of a user.

FIG. 1 shows a slow-recovery earplug 10 which includes a largely bullet-shaped main body portion 12 and a flanged rear portion 14. Thus, the earplug 10 of FIG. 1 is bell-shaped (although there are numerous other shapes providing effective seating within the ear canal, all of which are also included within the scope of this disclosure). In the embodiment of FIG. 1, the flanged rear portion 14 and the main body portion 12 are composed of the same material and form a unitary earplug. It should be understood, however, that the flange portion 14 could be formed of a separate material and joined to the main body 12 (using an adhesive, friction fit, or other attachment method or means known to those skilled in the art, by way of nonexclusive example). As indicated in FIG. 2, the main body portion 12 is designed so that it may be compressed (by rolling it down between the fingers, for example) to the configuration shown at 12A (in FIG. 2) so that it can be inserted into the ear canal C of a user. The main body portion 12 of the earplug would then expand to near its uncompressed configuration, pressing against the walls of the user's ear canal to create a snug fit to block noise. Alternatively, the earplug could be designed to be a press-in design which does not require roll-down for insertion. By way of non-exclusive example, such a press-in earplug might comprise a hollow foam shell and/or a stem with one or more foam flanges. The addition of PTFE into the foam could be beneficial for insertion of such press-in EarTips. Regardless, the outer surface of the main body portion 12 would be designed in shape and form and constructed to enable its reception in the ear and adapted to directly contact the surface of a user's ear canal. The earplug of FIG. 1 may have at least a main body portion 12 formed from slow recovery foam with PTFE distributed throughout, and in one preferred embodiment comprises slow recovery pressure-molded polyurethane foam with PTFE dispersed approximately uniformly throughout.

FIG. 3 shows an ear tip 50 of a sound transmission device, which when inserted into a user's ear canal would expand until securely positioned in the ear canal (forming a snug fit and an effective acoustical seal). The ear tip of FIG. 3 has a main body portion 51 designed to be somewhat cylindrical in shape (although other shapes providing effective seating within the ear canal are also included within the scope of this disclosure) and hollow (with an aperture therethrough), having an inner surface 53 designed and constructed to fit onto the stem or sound tube of a sound transmission device 57 (as shown in FIG. 4) and an outer surface 55 designed and constructed to enable its reception in the ear and adapted to directly contact the surface of a user's ear canal. As with the earplug 10 of FIG. 1, the ear tip 50 of FIG. 3 may be formed of foam with slow recovery properties having PTFE essentially distributed uniformly throughout its cell structure, and in the preferred embodiment shown in these figures would be formed of slow-recovery low resilient polyurethane foam with PTFE dispersed throughout.

Applicants have found that the addition of low coefficient of friction additive (such as PTFE by way of specific but non-exclusive example) to a slow-recovery polyurethane foam results in a finer, more uniform cell structure for the foam. The average cell size (as measured by diameter) of polyurethane foam with PTFE is noticeably reduced (when considering all cells across the entire cross-section of an eartip) when compared to the average cell size of control (standard) slow recovery foam without PTFE. Additionally, the cells in PTFE foam are of more uniform size and shape. In typical slow recovery polyurethane foam, the cells vary significantly in size throughout a cross-section of foam, with the cells near the center being significantly larger than the cells near the surface. In the typical slow recovery polyurethane foam, most cells nearest the surface have a diameter of about 0.05 to 0.1 mm diameter while most cells near the center have a diameter of over 0.2 mm diameter. Stated another way, in such typical foam earplugs the average cross-sectional area of cells near the surface is less than half the average cross-sectional area of cells near the center of the foam main body portion. Applicants have found, however, that in the PTFE enhanced slow recovery foam of FIG. 1, the difference in cell size across the cross-sectional width of the earplug is much less pronounced, resulting in a more uniform cell structure. In other words, in PTFE enhanced slow recovery polyurethane foam the average cross-sectional area of cells near the surface is greater than half the average cross-sectional area of cells near the center of the foam main body portion. Applicants have also found that the cell shape of PTFE enhanced foam is more uniform when compared to control foam without PTFE.

Applicants have found that this finer, more uniform cell structure provides many beneficial characteristics to PTFE foam EarTips. First, the EarTips of FIGS. 1 and 3 may offer a lower recovery pressure. This results in a more comfortable fit when users insert the EarTips, since the foam body 12 expands to snuggly fit within the ear canal but does not press on the ear canal with high pressures that might prove uncomfortable for long-term use. Such lower recovery pressure may allow for deeper insertion (since users feel more comfortable), thus offering the possibility of improved sound attenuation. Additionally, lower recovery pressure may allow for prolonged wearability. Internal testing by Applicants found that test subjects perceived that the present EarTips provide a softer feel and improved comfort, without as much perceived pressure, when compared to control earplugs (of slow recovery polyurethane foam without PTFE, such as Sperian's Max™ earplugs by way of example).

The EarTips of FIG. 3 may also provide reduced static electricity buildup when used with a sound transmission device. Some sound transmission devices may generate an electro-static charge during use. If such a static charge is allowed to build to a sufficiently high level, when it discharges it may cause users an unpleasant shock. Applicants have found that the PTFE enhanced slow recovery polyurethane foam EarTips of FIG. 3 may offer improved conductivity. Typical slow recovery polyurethane foam has a volume conductivity of about $6.8 \times 10^{-8}$ Sm-1, while the PTFE enhanced foam has a volume conductivity of about $6.8 \times 10^{-5}$ Sm-1. This improved conductivity may result from the finer cell structure provided by the addition of PTFE, which may provide for a better path of electrical conductivity. And by improving the conductivity provided by the EarTip of FIG. 3, the PTFE enhanced foam may serve to reduce electrostatic buildup by allowing for discharge of small amounts of electricity over time. In this way, the EarTip of FIG. 3 may help reduce unwanted shock to users of sound transmission devices. Further, the reduction of static buildup, along with the finer cell structure, may act to reduce soiling of the outer surface of the EarTip.

Applicants have also found that the EarTips of FIGS. 1 and 3 may roll down better, with fewer wrinkles. This may be beneficial since wrinkles tend to prevent EarTips from forming as effective a seal as possible (since the outer surface may not form a tight seal around the user's entire ear canal, offering a less resistive path for sound penetration), reducing the sound attenuation which may be provided by the EarTip. So again, this characteristic may improve effective insertion, providing for a snug fit that may improve sound attenuation in practice. Further, the improved dynamic coefficient of friction of PTFE enhanced EarTips may also improve effective press-in insertion.

Further, Applicants have found that the improved EarTips of FIGS. 1 and 3 may allow for improved insertion. In order for EarTips to function effectively (fitting snuggly in the user's ear canal to block unwanted outside noise), they should be properly inserted into the user's ear canal. If the EarTips do not slide easily in the ear canal during placement, it may be difficult for inexperienced users to properly insert the EarTips in place. More specifically, it may be difficult for users to insert the main body of the eartip sufficiently deeply in their ear canal if there is too much frictional resistance between the outer surface of the EarTip and the ear canal. Applicants have found that the EarTip embodiments of FIGS. 1 and 3 have a significantly lower kinetic coefficient of friction than other (standard) slow recovery polyurethane earplugs. By way of example, Applicants' testing has demonstrated that typical slow recovery polyurethane foam earplugs have an average kinetic coefficient of friction of about 1.80 to about 1.84, while the EarTips of embodiments shown in FIGS. 1 and 3 have an average kinetic coefficient of friction of about 1.21 to about 1.32. The table below provides the specific experimental test results (using an IMASS TL-2200 Slip/Peel Tester to compare five sample specimens), demonstrating the improved kinetic coefficient of friction performance of the embodiments of FIGS. 1 and 3.

The results of our measurements are tabulated below.

| Specimen | Static COF | Kinetic COF |
|---|---|---|
| Orange-1 | 1.21 | 1.67 |
| Orange-2 | 1.42 | 1.77 |
| Orange-3 | 1.55 | 1.93 |
| Orange-4 | 1.78 | 1.81 |
| Orange-5 | 1.49 | 1.82 |
| Orange Average(total) | 1.49 | 1.80 |
| Orange Average #2 | 1.49 | 1.84 |
| Vanilla-1 | 1.76 | 0.97 |
| Vanilla-2 | 1.97 | 2.03 |
| Vanilla-3 | 1.80 | 1.14 |
| Vanilla-4 | 1.91 | 1.47 |
| Vanilla-5 | 1.70 | 1.01 |
| Vanilla Average | 1.83 | 1.32 |
| Vanilla Average #2 | 1.82 | 1.21 |

Note:
Orange specimens are standard slow recovery foam samples, while vanilla specimens are PTFE enhanced slow recovery foam samples, and the first average is across all specimens, while average 2 results from eliminating the high and low values in an attempt to avoid anomalous readings.

Thus, the EarTips of FIGS. 1 and 3, enhanced with PTFE, offer less resistance to insertion (as demonstrated by the kinetic coefficient of friction results) and should slide better into place within the ear canal of a user than standard slow recovery foam (which is represented by the orange control sample specimens above). Applicants believe that this improvement in insertion (as seen by the lower coefficient of kinetic friction) results from a synergistic combination of the finer, more uniform cell structure, along with the surface characteristics of the PTFE itself. Applicants also note that the table above demonstrates an unusual phenomenon: while the addition of PTFE provides for a lower kinetic coefficient of friction, it simultaneously provides for a higher static coefficient of friction. This unexpected result further improves the real world usage characteristics of the EarTips of FIGS. 1 and 3. The lower kinetic coefficient of friction means that the EarTips are easier to insert, while the higher static coefficient of friction means that once inserted in place, the EarTips tend to stay in place. This factor can be quite important, since movement of the ear canal (as when the user talks or eats, and the jaw motion causes motion in the ear canal) may tend to dislodge the snug fit of the EarTips over time if they are not held in place adequately (such as by a high static coefficient of friction). Thus, the EarTips of FIGS. 1 and 3 offer both improved insertion (due to the lower kinetic coefficient of friction) and improved retention (due to the higher static coefficient of friction).

Applicants have also found that the EarTip of FIG. 1 may provide superior sound attenuation qualities. Internal testing by Applicants may indicate a relative improvement in the sound attenuation characteristics of the EarTip of FIG. 1 when compared to a control earplug of standard slow recovery polyurethane foam (without PTFE), such as Sperian's Max™ earplug. This improvement is particularly exciting since the control earplug is already rated at a very high NRR sound attenuation level. Thus, the EarTip shown in FIG. 1 may offer the highest available passive attenuation foam earplugs to date. These improvements may result at least partially from the improved insertability (since the eartips may allow for deeper insertion and a better seal), but may also result at least partially from the physical properties of the PTFE enhanced foam. Regardless, the sound attenuation characteristics associated with the EarTip of FIG. 1 offer attractive possibilities.

In one embodiment, the EarTip is pressure molded from slow recovery urethane foam material. This is accomplished by mixing the foam materials (along with the PTFE), placing them in a mold having a cavity shaped to produce the desired EarTip shape, and closing the mold, with a very small opening for escape of air such as a slit of about 0.2 millimeters width. The amount of foamable material is sufficient to fill a cavity of a volume greater than that of the finished EarTip, so the material expands to the full size of the cavity and then presses with considerable pressure against the walls of the cavity. Sufficient foamable material is present that the pressure of the expanding foam against the mold walls is at least 0.5 psi. More preferably, the pressure would be about 2 psi. This process is not limited exclusively to slow recovery polyurethane foam, but is merely exemplary, and could also be used with other slow recovery foam. Alternatively, EarTips formed from slow recovery urethane foam with PTFE could be molded in an open mold.

In another embodiment, the low coefficient of friction additive may have characteristics so that it migrates outward over time. This could serve to provide a surface lubrication feature that inherently replenished itself over time, resulting in a more lasting surface lubrication treatment. The degree of migration (such as the rate at which the additive might ooze outward to the surface) may depend on the foam structure and characteristics, as well as the characteristics inherent in the additive.

The addition of PTFE into the polyurethane slow recovery foam may produce a foam having a finer, more uniform cell structure. In other words, the cells of this foam will be smaller, have a more regular shape, and have less size differentiation across the cross-section than typical polyurethane foam cells. This finer, more uniform cell structure may result in lower recovery pressure, a smoother outer skin, reduced electro-static buildup, improved insertion and retention, and/or an improved attenuation rating. The combination of high attenuation with ease of insertion makes the present EarTip particularly attractive, especially in light of its comfort features. Thus, such eartips may offer characteristics leading to improved performance and user satisfaction.

While specific examples set forth above relate to EarTips, it should be understood that this disclosure is not limited to such applications. Indeed, the slow recovery low resilient foam plastic material with PTFE described above could be used for other purposes and devices in which its characteristics would be beneficial, and all such uses are included within the scope of this disclosure. The figures discussed above provide examples of various exemplary devices, systems, and techniques and ways to make and use such devices. These illustrations are merely exemplary. The scope of the present disclosure extends beyond the specific examples set forth above, capturing the full range of the inventive concept (and including all equivalents).

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Accordingly, the scope of protection is not limited by the description set out above, but is defined by the claims which follow, that scope including all equivalents of the subject matter of the claims. Furthermore, any advantages and features described above may relate to specific embodiments but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings refer to a "Field of the Invention," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. The term "comprising" as used herein is to be construed broadly to mean including but not limited to, and in accordance with its typical usage in the patent context, is indicative of inclusion rather than limitation (such that other elements may also be present). In all instances, the scope of the claims shall be considered on their own merits in light of this disclosure, but should not be constrained by the headings set forth herein.

What is claimed is:

1. An EarTip comprising:
a main body portion constructed to enable its reception in an ear canal,
the main body portion being formed of pressure-molded slow recovery low resilient foam plastic material that comprises:
slow recovery low resilient polyurethane foam with cell structures that have a low coefficient of friction additive distributed throughout each of the cell structures, and
multiple gas-filled open cells defined by the cell structures,
wherein a plurality of the cell structures form a skin on an exterior of the EarTip, and
wherein the low coefficient of friction additive distributed throughout each of the cell structures comprises PTFE.

2. The EarTip of claim 1 wherein the foam is formed by:
providing a prepolymer stream and a latex aqueous solution stream;
adding between 2 to 7% by weight PTFE to the latex aqueous solution stream; and
mixing, in a closed mold under at least 0.5 pounds per square inch of pressure, the prepolymer stream and the latex aqueous solution stream, wherein the latex aqueous solution stream comprises at least 60% solids.

3. The EarTip of claim 1, wherein the main body portion comprises a hollow foam shell, and wherein the hollow foam shell of the main body is configured to directly contact the ear canal without any intervening material between the ear canal and the foam.

4. The EarTip of claim 1 wherein the slow recovery low resilient polyurethane foam is latex-modified polyurethane foam.

5. The EarTip of claim 1 wherein the additive is approximately uniformly distributed throughout the cell structures of the foam plastic material.

6. The EarTip of claim 1 wherein the main body portion forms an earplug.

7. The Ear Tip of claim 1 wherein the main body portion comprises an aperture therethrough, the aperture being operable to receive a sound tube.

8. An EarTip comprising:
a main body portion constructed to enable its reception in an ear canal,
the main body being formed of pressure-molded slow recovery low resilient foam plastic material comprising:
slow recovery low resilient polyurethane foam with cell structures that have a low coefficient of friction additive distributed throughout the cell structure, and
multiple gas-filled open cells defined by the cell structures,
wherein the main body portion has a static coefficient of friction greater than 1.70 and a kinetic coefficient of friction less than 1.47.

9. An EarTip comprising a main body portion constructed to enable its reception in an ear canal, wherein:
the main body is formed of slow recovery low resilient foam plastic material comprising multiple open cells defined by cell structures that have low coefficient of friction additive distributed throughout the cell structures;
the average diameter of the cells is smaller than that of standard slow recovery low resilient foam plastic without additive, wherein the additive comprises PTFE; and
the main body has a cross-section, wherein the average diameter of the cells does not vary across the cross-section as much as that of standard slow recovery low resilient foam plastic without additive.

10. The EarTip of claim 9, wherein the foam is formed by:
providing a prepolymer stream and a latex aqueous solution stream;
adding between 2 to 7% by weight PTFE to the latex aqueous solution stream; and
mixing the prepolymer stream and the latex aqueous solution stream, wherein the latex aqueous solution stream comprises at least 60% solids and materials in the prepolymer stream and the latex aqueous solution stream foam under pressure in a closed mold.

* * * * *